US012559773B2

(12) United States Patent
Yamanishi et al.

(10) Patent No.: US 12,559,773 B2
(45) Date of Patent: Feb. 24, 2026

(54) BUBBLE EJECTION METHOD, BUBBLE EJECTING DEVICE, AND BUBBLE EJECTION APPARATUS

(71) Applicant: KYUSHU UNIVERSITY, NATIONAL UNIVERSITY CORPORATION, Fukuoka (JP)

(72) Inventors: Yoko Yamanishi, Fukuoka (JP); Yu Yamashita, Fukuoka (JP); Keita Ichikawa, Fukuoka (JP); Yudai Fukuyama, Fukuoka (JP); Ren Masuda, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 1217 days.

(21) Appl. No.: 17/288,693

(22) PCT Filed: Oct. 21, 2019

(86) PCT No.: PCT/JP2019/041260
§ 371 (c)(1),
(2) Date: Apr. 26, 2021

(87) PCT Pub. No.: WO2020/085281
PCT Pub. Date: Apr. 30, 2020

(65) Prior Publication Data
US 2021/0395782 A1     Dec. 23, 2021

(30) Foreign Application Priority Data

Oct. 26, 2018    (JP) ................................ 2018-202368

(51) Int. Cl.
*C12N 15/89*     (2006.01)
*B01L 5/00*     (2006.01)
(Continued)

(52) U.S. Cl.
CPC .............. *C12N 15/895* (2013.01); *B01L 5/00* (2013.01); *C12M 47/06* (2013.01);
(Continued)

(58) Field of Classification Search
CPC ...... C12N 15/895; C12N 15/87; C12M 47/06; C12M 35/02; C12M 35/04; C12M 23/26;
(Continued)

(56) References Cited

U.S. PATENT DOCUMENTS 3,177,800 A * 4/1965 Frazer .................. B41J 2/14096
347/61
3,179,042 A * 4/1965 Naiman ............... B41J 2/14096
347/61
(Continued)

FOREIGN PATENT DOCUMENTS

EP        3202884 A1     8/2017
JP     2009-527321 A     7/2009
(Continued)

OTHER PUBLICATIONS

Japanese Office Action dated Sep. 4, 2023 issued in the corresponding Japanese Patent Application No. 2020-553380, with English machine translation.
(Continued)

*Primary Examiner* — Brian K Talbot
(74) *Attorney, Agent, or Firm* — Rimon P.C.

(57) ABSTRACT

The present invention addresses the problem of providing a bubble ejection method based on a new principle that is different from conventional bubble ejection methods and a bubble ejecting device.
To solve the problem, provided is a bubble ejection method using a bubble ejecting device, wherein the bubble ejecting device comprises
a substrate formed of a dielectric,
(Continued)

10 at least one bubble ejection hole formed so as to penetrate through a first face and a second face, which is a face opposite to the first face, of the substrate, a first opening formed at a position of the first face at which the bubble ejection hole penetrates, and a second opening formed at a position of the second face at which the bubble ejection hole penetrates, the bubble ejection method comprising:

a substrate-conductive liquid contact step;

a conductive liquid-electrode contact step;

a voltage application step; and a bubble ejection step.

19 Claims, 9 Drawing Sheets

(51) Int. Cl.
*C12M 1/00* (2006.01)
*C12M 1/42* (2006.01)

(52) U.S. Cl.
CPC ...... *B01L 2400/0442* (2013.01); *C12M 23/26* (2013.01); *C12M 35/02* (2013.01); *C12M 35/04* (2013.01)

(58) Field of Classification Search
CPC .... C12M 15/87; B01L 5/00; B01L 2400/0442
USPC ..................................................... 427/421.1
See application file for complete search history.

(56) References Cited

U.S. PATENT DOCUMENTS

| | | | | |
|---|---|---|---|---|
| 4,275,290 | A * | 6/1981 | Cielo | ................... B41J 2/14137 |
| | | | | 347/61 |
| 4,546,360 | A * | 10/1985 | Fischbeck | ........... B41J 2/14096 |
| | | | | 347/61 |
| 7,704,743 | B2 | 4/2010 | Fedorov et al. | |
| 8,101,169 | B2 | 1/2012 | Chalberg, Jr. et al. | |
| 10,716,610 | B2 | 7/2020 | Yamanishi et al. | |
| 2010/0227408 | A1 * | 9/2010 | Vankov | ................. C12N 13/00 |
| | | | | 435/173.6 |
| 2017/0292105 | A1 * | 10/2017 | Yamanishi | ............... A01G 7/06 |
| 2017/0306284 | A1 | 10/2017 | Yamanishi et al. | |
| 2018/0305654 | A1 * | 10/2018 | Yamanishi | .............. G03F 7/162 |
| 2020/0240031 | A1 * | 7/2020 | Yamanishi | .......... C23C 18/1669 |
| 2020/0337757 | A1 | 10/2020 | Yamanishi et al. | |
| 2021/0292692 | A1 * | 9/2021 | Makabe | ................. C12N 15/87 |

FOREIGN PATENT DOCUMENTS

| | | | |
|---|---|---|---|
| WO | 2013/129657 | A1 | 9/2013 |
| WO | 2016/052511 | A1 | 4/2016 |
| WO | 2017/069085 | A1 | 4/2017 |

OTHER PUBLICATIONS

English Translation of the Written Opinion of the International Search Authority mailed Jan. 7, 2020, in International Application No. PCT/JP2019/041260.

The Extended European Search Report issued in corresponding European Application No. 19876976.2, dated Nov. 18, 2021.

* cited by examiner 1, 1a

BUBBLE EJECTION METHOD, BUBBLE EJECTING DEVICE, AND BUBBLE EJECTION APPARATUS

CROSS REFERENCE TO RELATED APPLICATIONS

This application is the U.S. National Phase under 35 U.S.C. § 371 of International Application No. PCT/JP2019/041260, filed on Oct. 21, 2019, which in turn claims the benefit of Japanese Application No. 2018-202368, filed on Oct. 26, 2018, the entire contents of each are hereby incorporated by reference.

TECHNICAL FIELD

The present disclosure in the present application relates to a bubble ejection method, a bubble ejecting device, and a bubble ejection apparatus.

BACKGROUND ART

Due to progress of biotechnology in recent years, there is a growing demand for local processing of a cell or the like, such as processing to perforate a membrane or a wall of a cell and remove a nucleus from the cell or introduce a nucleic acid substance such as DNA to the cell. As a local processing technology (hereafter, also referred to as "local ablation method"), methods using a contact processing technology using a probe such as an electrical scalpel, a contactless ablation technology using laser or the like, or the like are widely known.

In a conventional contact processing technology using a probe such as an electrical scalpel, however, there are problems that (1) because of a nature of burning off a target by Joule heat generated at a continuous high frequency, a peripheral tissue is much affected by roughness of the cut surface and heat invasion due to heat, in particular, the cut surface is much damaged by heat in a case of processing of a biomaterial in a liquid phase, (2) protein denaturation or amide bound fragmentation causes difficulty in recombination or regeneration, and (3) further in the continuous processing, adsorption of heat-denatured proteins or the like or adsorption of bubbles generated due to heat to the probe significantly deteriorates an observation environment of an incision surface, which makes high degradability processing difficult.

Further, also in a contactless processing technology using laser such as femtosecond laser, there is a problem of difficulty in continuous processing or the like because locally spotted high-density energy causes the heat to affect the tissue around a cut surface and, in particular, because of generation of bubbles or the like due to heat generated at processing in a case of processing of a target in a liquid phase.

On the other hand, as a local physical injection technology for introducing an injection substance such as a nucleic acid substance to a cell or the like (hereafter, also referred to as "local injection"), an electroporation, a sonoporation technology using ultrasonic waves, a particle gun method, and the like are widely known. In the conventional electroporation technology, however, there is a limit in improving permeability of a cell membrane by changing the electric field intensity, and there are problems of difficulty in injection to a target having a hard cell membrane or a cell wall instead of soft fatty double membranes, difficulty in local injection to an intended place due to restriction of the arrangement of electrodes or the like, and the like. Further, in the sonoporation technology using ultrasonic waves, there are problems of difficulty in convergence of ultrasonic waves, difficulty in generating local cavitation of bubbles to increase resolution, and the like. Furthermore, in an injection method with the particle gun method, there is a problem of low introduction efficiency or the like because substances attached to particle surfaces are detached from the surfaces when particles are injected.

As a method (device) to solve the problems described above, it is known that a bubble ejection member including a core formed of a conductive material; a shell portion formed of an insulating material, covering the core, and including a portion extending from the tip of the core; and an airgap formed between the extending portion of the shell portion and the tip of the core are produced, and it is possible to cut (perform local ablation on) a processing target by immersing the bubble ejection member in a solution, applying a high frequency voltage to the solution to generate bubbles, continuously emitting the bubbles to the processing target (see Patent Literature 1). Further, a bubble ejection chip on which a plurality of electrodes formed of a conductive material and bubble ejection portions formed so as to interpose the electrode are formed on a substrate is known (see Patent Literature 2).

CITATION LIST

Patent Literature

Patent Literature 1: International Publication No. WO 2013/129657
Patent Literature 2: International Publication No. WO 2016/052511

SUMMARY OF INVENTION

Technical Problem

The bubble ejection member disclosed in Patent Literature 1 is produced by inserting electrodes in an insulating material such as glass and heating, pulling, and cutting off the insulating material and the electrode so that the circumference of an electrode is covered with the insulating material due to a difference in viscoelasticity between the insulating material and the electrode and the insulating material is extended beyond the tip of the electrode. Thus, since the tip portion that is the extending part of the insulating material, that is, a bubble ejection port is very narrow and thin, there is a problem of easy breakage. Further, since the bubble ejection port is very narrow and thin, there is a problem of the bubble ejection port being likely to damage a processing target in processing of the processing target such as a cell.

Further, the bubble ejection chip disclosed in Patent Literature 2 is produced by using a semiconductor lithography technology. Therefore, any number of bubble ejection portions having any size of the bubble ejection port can be formed on a substrate. Thus, advantageously, the bubble ejection chip is less likely to break, and it is easier to adjust the size of the bubble ejection port compared to the bubble ejection member disclosed in Patent Literature 1. However, the bubble ejection chip disclosed in Patent Literature 2 is produced by a semiconductor lithography technology and thus has a problem of a complex production process.

The present disclosure has been made in order to solve the problems described above, and according to a thorough study, it has been newly found that, (1) by using a bubble ejecting device including: a substrate formed of a dielectric; and a bubble ejection hole formed so as to penetrate through a first face and a second face, which is a face opposite to the first face, of the substrate and (2) by applying a voltage between a first electrode and a second electrode with a conductive liquid and the bubble ejection hole being in contact with each other, (3) it is possible to eject a bubble from the bubble ejection hole into the conductive liquid.

That is, the object of the present disclosure is to provide a bubble ejection method, a bubble ejecting device used for the bubble ejection method, and a bubble ejection apparatus including the bubble ejecting device based on a novel principle that is different from that for the conventional bubble ejection method using the bubble ejection member (bubble ejection chip).

Solution to Problem

The present disclosure relates to a bubble ejection method, a bubble ejecting device, and a bubble ejection apparatus illustrated below.

(1) A bubble ejection method using a bubble ejecting device, wherein the bubble ejecting device comprises a substrate formed of a dielectric, at least one bubble ejection hole formed so as to penetrate through a first face and a second face, which is a face opposite to the first face, of the substrate, a first opening formed at a position of the first face at which the bubble ejection hole penetrates, and a second opening formed at a position of the second face at which the bubble ejection hole penetrates, the bubble ejection method comprising:

a substrate-conductive liquid contact step of bringing a portion including at least the first opening and the second opening into contact with a conductive liquid;

a conductive liquid-electrode contact step of bringing a first electrode into contact with the conductive liquid on the first opening side and bringing a second electrode into contact with the conductive liquid on the second opening side;

a voltage application step of applying a voltage between the first electrode and the second electrode; and a bubble ejection step of ejecting a bubble from the bubble ejection hole into the conductive liquid.

(2) The bubble ejection method according to (1) above, wherein at least two or more bubble ejection holes are formed.

(3) The bubble ejection method according to (1) or (2) above, wherein a size of the first opening and a size of the second opening are different from each other.

(4) The bubble ejection method according to any one of (1) to (3) above, wherein a dielectric strength of the dielectric is greater than or equal to 10 MV/m.

(5) The bubble ejection method according to any one of (1) to (4) above, wherein the substrate is formed of a flexible material.

(6) A bubble ejecting device comprising:

a substrate formed of a dielectric;

at least one bubble ejection hole formed so as to penetrate through a first face and a second face, which is a face opposite to the first face, of the substrate;

a first opening formed at a position of the first face at which the bubble ejection hole penetrates; and a second opening formed at a position of the second face at which the bubble ejection hole penetrates.

(7) The bubble ejecting device according to (6) above, wherein at least two or more bubble ejection holes are formed.

(8) The bubble ejecting device according to (6) or (7) above, wherein a size of the first opening and a size of the second opening are different from each other.

(9) The bubble ejecting device according to any one of (6) to (8) above, wherein a dielectric strength of the dielectric is greater than or equal to 10 MV/m.

(10) The bubble ejecting device according to any one of (6) to (9) above, wherein the substrate is formed of a flexible material.

(11) The bubble ejecting device according to any one of (6) to (10) above further comprising a first chamber and a second chamber, wherein the first chamber includes a portion including at least the first opening in the first face of the substrate, and a chamber first member arranged in contact with the first face, wherein filling a conductive liquid in the first chamber enables the first opening to be in contact with the conductive liquid, and wherein the second chamber includes a portion including at least the second opening in the second face of the substrate, and a chamber second member arranged in contact with the second face, wherein filling a conductive liquid in the second chamber enables the second opening to be in contact with the conductive liquid.

(12) The bubble ejecting device according to any one of (6) to (11) above further comprising:

a first electrode arranged in the first chamber; and a second electrode arranged in the second chamber.

(13) A bubble ejection apparatus comprising:

the bubble ejecting device according to any one of (7) to (12) above; and an electric output mechanism for ejecting a bubble from the bubble ejecting device.

Advantageous Effect of Invention

The bubble ejecting device disclosed in the present application can be easily produced by forming a bubble ejection hole in a substrate formed of a dielectric so as to penetrate the substrate. Further, since the bubble ejection hole is formed so as to penetrate the substrate, a bubble is ejected from the surface of the substrate. Thus, unlike the conventional bubble ejection port, the bubble ejection hole is less likely to break. Therefore, usability in handling the bubble ejecting device when the bubble ejection method is implemented is improved.

BRIEF DESCRIPTION OF DRAWINGS

FIG. 5A is a top view of a device 1d according to a fourth embodiment, and FIG. 5B is a sectional view taken along a line X-X' of FIG. 5A. FIG. 5C is a top view of a modified example of a device 1d, and FIG. 5D is a sectional view taken along a line X-X' of FIG. 5C.

FIG. 9A is a photograph of a device of Example 2 captured from the top, and FIG. 9B is a photograph taken after electrical output in which dotted circles illustrate grown bubbles.

FIG. 10A is a photograph from a first opening side taken when a device of Example 3 is used, and FIG. 10B is a photograph from a first opening side taken when a device of Example 4 is used in which a circular portion surrounded by a white line of the photograph represents an ejected bubble.

FIG. 11A is a photograph taken immediately after electric output, and FIG. 11B is a photograph taken after a while of electrical output in Example 5.

FIG. 12A is a photograph taken before a voltage is applied, FIG. 12B is a photograph taken after a voltage of 450 V is applied, FIG. 12C is a photograph taken after a voltage of 650 V is applied, and FIG. 12D is a photograph taken after a voltage of 750 V is applied in Example 6.

FIG. 13A is a photograph of a device of Example 7 taken after a while of application of a voltage, and FIG. 13B is a photograph of a device of Example 8 taken after a while of application of a voltage.

FIG. 14A is a photograph of the first opening side taken before a voltage is applied, and FIG. 14B is a photograph taken after the voltage is applied in Example 9.

DESCRIPTION OF EMBODIMENTS

A bubble ejection method, a bubble ejecting device (hereafter, also simply referred to as a "device"), and a bubble ejection apparatus will be described below in detail with reference to the drawings. Note that, in the present specification, members having similar functions are labeled with the same or similar references. Further, repeated description of the members labeled with the same or similar references may be omitted. Further, the numerical values disclosed in the present specification is not intended to mean only the numerical value of interest in a strict sense but may include a positive or negative error as long as it is within a range that enables the advantageous effect disclosed in the present application. Similarly, reference to "about" does not mean only the numerical value of interest in a strict sense but may include a positive or negative error as long as it is within a range that enables the advantageous effect disclosed in the present application.

First Embodiment of Device

Figure 1:
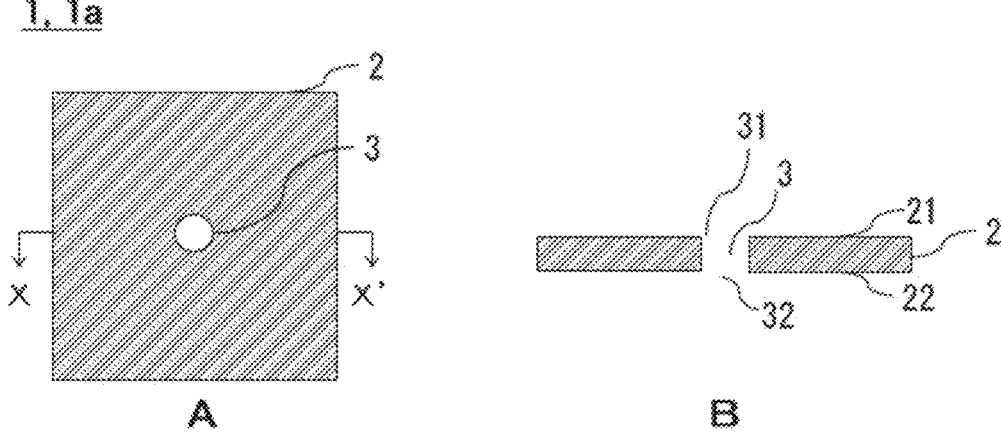
FIG. 1A is a top view of a device 1a according to a first embodiment.
FIG. 1B is a sectional view taken along a line X-X' of FIG. 1A.

A device 1a according to a first embodiment will be described with reference to FIG. 1. FIG. 1A is a top view of the device 1a, and FIG. 1B is a sectional view taken along a line X-X' of FIG. 1A. The device 1a includes a substrate 2 formed of a dielectric and a bubble ejection hole 3. The bubble ejection hole 3 is formed so as to penetrate through a first face 21 and a second face 22, which is a face opposite to the first face 21, of the substrate 2, a first opening 31 is formed in the first face 21, and a second opening 32 is formed in the second face 22.

Before describing the configuration of the device 1a in detail, the principle of how a bubble is ejected by using the device 1a will be described first. FIG. 2A to FIG. 2D are schematic sectional views illustrating the principle of how a bubble B is ejected. Note that, since the components of the device 1a are the same in these four drawings, denotation of references other than the bubble B is omitted in FIG. 2B to FIG. 2D.

Figure 2:
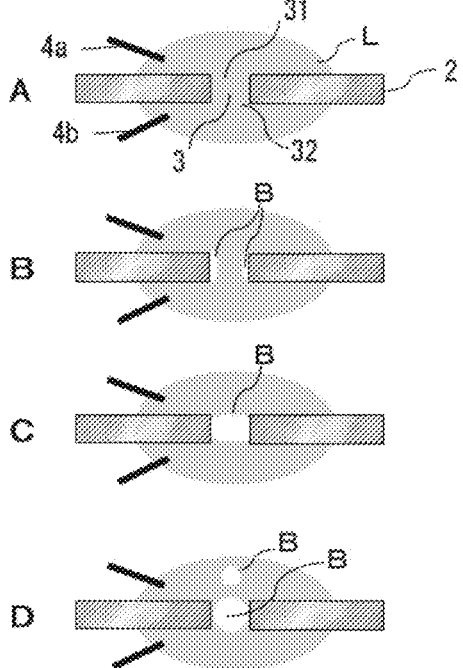
FIG. 2A to FIG. 2D are schematic sectional views illustrating the principle of how a bubble B is ejected.

As illustrated in FIG. 2A, before a bubble is ejected, first, at least the periphery of the first opening 31 and the second opening 32 is brought into contact with a conductive liquid L that is a conductive fluid. The conductive liquid L permeates in the bubble ejection hole 3 by capillary force. Next, a first electrode 4a is brought into contact with the conductive liquid L on the first opening 31 side, a second electrode 4b is brought into contact with the conductive liquid L on the second opening 32 side, and an electric output mechanism (not illustrated) is connected to the first electrode 4a and the second electrode 4b by electric wires or the like. Next, when a voltage is applied between the first electrode 4a and the second electrode 4b, the bubble B is generated on the circumferential part of the bubble ejection hole 3 as illustrated in FIG. 2B, and the generated bubble B grows so as to close the bubble ejection hole 3 as illustrated in FIG. 2C. The bubble B that has continuously grown is then ejected into the conductive liquid L, as illustrated in FIG. 2D.

It is considered that the bubble B is ejected as illustrated in FIG. 2A to FIG. 2D by using the device 1a because the substrate 2 does not conduct electricity but accumulates electricity and thereby an electric field occurs around the bubble ejection hole 3. Thus, it is desirable that the substrate 2 be formed of a dielectric that is a material through which no current or negligibly small current flows and which causes an electric field to occur. The material forming the substrate 2 may be a known dielectric material, for example, a thermoplastic resin, a thermosetting resin, a UV-curing resin, a glass, a ceramic, a mica (isinglass), or the like. Note that, when the size of the first opening 31 or the second opening 32 of the bubble ejection hole 3 described later is relatively large, a relatively large voltage will be applied in order to eject the bubble B from the bubble ejection hole 3. When dielectric breakdown is then caused by the applied voltage, this may undesirably cause a change in the size of the bubble ejection hole 3 (the first opening 31 and/or the second opening 32) or damage of the substrate 2. Therefore, while depending on the thickness of the substrate 2 and/or the size of the bubble ejection hole 3, the material forming the substrate 2 may be a material whose dielectric strength is 4 MV/m or higher, 5 MV/m or higher, 6 MV/m or higher, 7 MV/m or higher, 8 MV/m or higher, 9 MV/m or higher, or 10 MV/m or higher, for example.

The material whose dielectric strength is 10 MV/m or higher may be, for example, polyimide (23 MV/m), polystyrene (20 to 28 MV/m), a glass (20 to 40 MV/m), an epoxy resin (without a filler, 11.8 to 19.6 MN/m), an epoxy resin (with a silica filler, 11.8 to 19.6 MN/m), an epoxy resin (with a glass fiber filler, 11.8 to 15.7 MV/m), or the like, however, other materials than are listed above as examples may be used. Note that there is no particular upper limit for the dielectric strength.

The thickness of the substrate 2, in other words, the length in the penetration direction of the bubble ejection hole 3 is not particularly limited as long as it is in a range that enables ejection of a bubble, and the lower limit value may be, for example, 0.1 μm or larger or 1 μm or larger. Further, the upper limit value may be 1 cm or smaller, 5 mm or smaller, 1 mm or smaller, 500 μm or smaller, 200 μm or smaller, or 100 μm or smaller. Note that the thickness of the substrate 2 may be even or may be uneven. When the thickness of the substrate 2 is uneven, the lower limit value and the upper limit value described above are defined by the thickness of the substrate of a portion forming the bubble ejection hole 3, and the thickness of the substrate 2 other than the portion forming the bubble ejection hole 3 may be out of a range from the upper limit value to the lower limit value described above.

Further, the substrate 2 may be formed to have flexibility, while the flexibility may vary in accordance with a combination of the material and the thickness of the substrate 2. The substrate 2 having flexibility is advantageous in that, in ablation of the processing target using the device 1a, the device 1a can be brought into contact with a processing target even when the processing target is a plant, an animal skin, or the like and is curved, for example. A material having high flexibility may be, for example, polyimide or the like.

The shape of the bubble ejection hole 3 is not particularly limited as long as it can eject a bubble. When the first opening 31 and the second opening 32 are viewed in a cross-section view parallel to the first face 21 or the second face 22 of the bubble ejection hole 3, for example, when the shape thereof is viewed, the shape may be a circle, an ellipse, a polygonal having three or more angles, or the like. Further, in a cross-section view perpendicular to the first face 21 or the second face 22, for example, in a cross-section view illustrated in FIG. 1B, a line connecting the first opening 31 to the second opening 32 may be a straight line as with the example illustrated in FIG. 1B or may be non-linear such as a curve, a step-wise shape, or the like. Note that, although the first opening 31 and the second opening 32 have the same shape, that is, the bubble ejection hole 3 has a cylindrical shape having an even diameter in the example illustrated in FIG. 1A and FIG. 1B, the first opening 31 and the second opening 32 may have different shapes.

The size of the first opening 31 and the second opening 32 is not particularly limited as long as the conductive liquid L can enter the bubble ejection hole 3 by capillary force and a bubble can be ejected. If the bubble ejection hole 3 has the first opening 31 and the second opening 32 that are circles of the same size, that is, the bubble ejection hole 3 is a cylindrical shape, the lower limit value of the diameter of the first opening 31 and the second opening 32 can be, for example, 0.1 μm or larger, 0.5 μm or larger, 1 μm or larger, 2 μm or larger, or 5 μm or larger. Further, because an excessively large first opening 31 or second opening 32 requires a larger applied voltage, the upper limit value of the diameter of the first opening 31 and the second opening 32 can be 500 μm or smaller, 400 μm or smaller, 300 μm or smaller, 200 μm or smaller, or 100 μm or smaller. Note that, when the shape of the first opening 31 and the second opening 32 is other than a circle, the same diameter as described above may apply to the diameter of the circumscribed circle of the shape other than a circle. Note that, when the size of the first opening 31 and the second opening 32 is reduced, a hydrophilization treatment may be applied to the substrate 2 if necessary so that the conductive liquid L can easily enter the bubble ejection hole 3. The hydrophilization treatment can be performed by a treatment with a known method such as a plasma treatment.

A method of forming the bubble ejection hole 3 is not particularly limited as long as the bubble ejection hole 3 is formed so as to penetrate through the first face 21 and the second face 22 of the substrate 2. For example, the bubble ejection hole 3 can be formed by a known method such as a method of forming a through hole by using a drill, a method of etching covered with a mask, or the like.

Second Embodiment of Device

Figure 3:
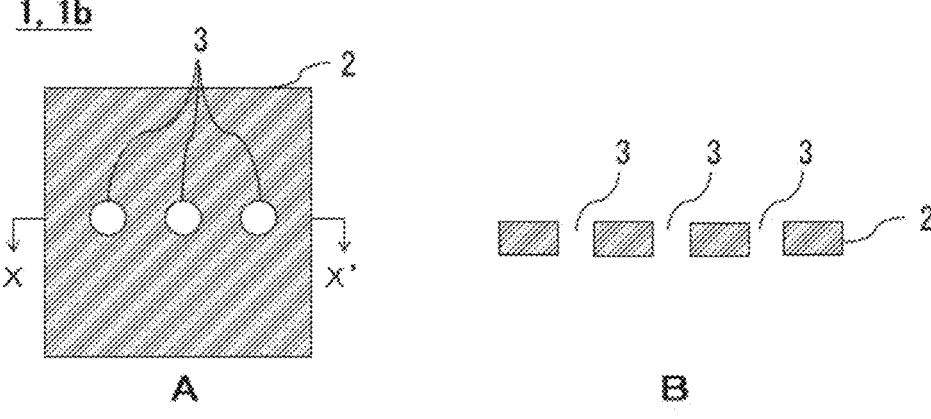
FIG. 3A is a top view of a device 1b according to a second embodiment.
FIG. 3B is a sectional view taken along a line X-X' of FIG. 3A.

Next, a device 1b according to a second embodiment will be described with reference to FIG. 3. FIG. 3A is a top view of the device 1b, and FIG. 3B is a sectional view taken along a line X-X' of FIG. 3A. The device 1b is different from the device 1a according to the first embodiment in that at least two bubble ejection holes 3 are formed and is the same as the device 1a with respect to other features. Note that, although an example in which the three bubble ejection holes 3 are arranged in series is illustrated in FIG. 3A and FIG. 3B, the number of bubble ejection holes 3 is not limited, and the arrangement of the bubble ejection hole 3 can be determined as appropriate in accordance with the purpose. With a use of the device 1b, bubbles can be ejected to different positions on a processing target at the same time.

Note that Patent Literature 2 discloses that a plurality of bubble ejection portions are formed and bubbles are ejected to different positions on a processing target at the same time. However, the chip disclosed in Patent Literature 2 is produced by using a photolithography technology. Thus, when the chips are manufactured in a manufacturing factory, while it is possible to adjust the arrangement or the like of a bubble ejection port by using a photomask of a particular shape, it is difficult to change the number or the arrangement of bubble ejection portions at a site of use. On the other hand, the device 1b is based on a different bubble ejection principle (apparatus) from that in Patent Literature 2, and in addition, the bubble ejection hole 3 can be easily formed by using a drill or the like. Therefore, it is possible to adjust the arrangement of the bubble ejection holes 3 if necessary at a site of use.

Third Embodiment of Device

Figure 4:
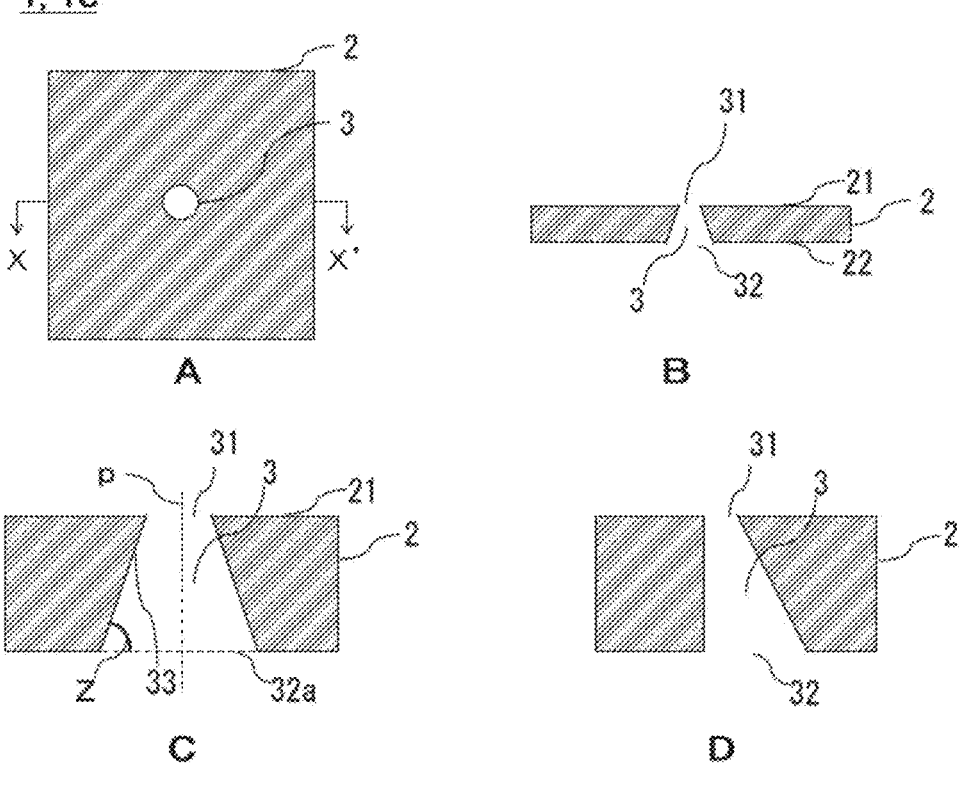
FIG. 4A is a top view of a device 1c according to a third embodiment.
FIG. 4B is a sectional view taken along a line X-X' of FIG. 4A.
FIG. 4C and FIG. 4D are diagrams illustrating a difference in size between a first opening 31 and a second opening 32 when a taper is formed.

Next, a device 1c according to a third embodiment will be described with reference to FIG. 4. FIG. 4A is a top view of the device 1c, and FIG. 4B is a sectional view taken along a line X-X' of FIG. 4A. The device 1c differs from the device 1a according to the first embodiment in that the device 1c is produced so that the first opening 31 and the second opening 32 have different sizes. Note that, in the present specification, the term "size" means a diameter in a case of a circle or a diameter of a circumscribed circle in a case of a shape other than a circle. Although the size of the first opening 31 is smaller than the size of the second opening 32 in the example illustrated in FIG. 4B, the size of the first opening 31 may be larger than the size of the second opening 32. Note that, in the present specification, the bubble ejection hole 3 formed such that the first opening 31 and the second opening 32 have different sizes may be referred to as "tapered" one. Further, the cylindrical or prismatic bubble ejection hole 3 in which the first opening 31 and the second opening 32 have the same shape and size may be referred to as "non-tapered" one.

As illustrated in Examples described later, in the case of the device 1a having substantially the same shape of the first opening 31 and the second opening 32, the bubble B that has grown in the bubble ejection hole 3 is discharged in a direction from a positive electrode to a negative electrode, where one of the first electrode 4a and the second electrode 4b is defined as the positive electrode, and the other is defined as the negative electrode. On the other hand, in the device 1c according to the third embodiment, a bubble is ejected from the smaller-sized one of the first opening 31 and the second opening 32 regardless of the direction of the positive electrode or the negative electrode. It is considered that this is because the smaller-sized opening part of the first opening 31 or the second opening 32 has a larger resistance than the larger-sized opening part and is subjected to a large voltage, and thus a bubble is generated in a direction of the smaller-sized opening.

A method of forming the tapered bubble ejection hole 3 is not particularly limited as long as a taper can be formed. For example, the method may be a method of producing the tapered bubble ejection hole 3 using a 3D printer; a method of forming a taper-shaped mold, pouring a thermosetting resin, a photo-curing resin, or UV curable resin, or the like or a melted thermoplastic resin into the mold, and separating the mole after the resin is cured; a method of laser cut processing; or the like.

The difference in size between the first opening 31 and the second opening 32 when a taper is formed will be described with reference to FIG. 4C. FIG. 4C illustrates an example of a case where the first opening 31 is circular, the second opening 32 is circular and has a larger diameter than the first opening 31, and a virtual line p connecting the center of the circle of the first opening 31 and the center of the circle of the second opening 32 is substantially orthogonal to a virtual plane 32a of the second opening 32. In the example illustrated in FIG. 4C, when the angle of a wall face 33 (a wall face line 33 in the cross-section view) of the bubble ejection hole 3 relative to the virtual plane 32a (a virtual line 32a in the cross-section view) of the second opening 32 is defined as Z, the upper limit value of Z can be smaller than 90 degrees. Further, the lower limit value of Z can be larger than 0 degree in principle and may be, for example, 1 degree, 5 degrees, 30 degrees, or 60 degrees.

Aside from the angle described above, when the area of the first opening 31 is defined as 1, the area of the second opening 32 can be larger than 1 and smaller than or equal to 10,000, smaller than or equal to 5,000, smaller than or equal to 1,000, smaller than or equal to 500, smaller than or equal to 100, or smaller than or equal to 50, for example. When the shape of the first opening 31 and the second opening 32 is other than a circle, for example, when the shape is an ellipse, a polygonal, or the like, the area ratio between the first opening 31 and the second opening 32 can be the same ratio as that in a case where the shape is a circle.

In the example illustrated in FIG. 4C, while the bubble ejection hole 3 is symmetrical about the virtual line p in a cross-section view, the shape of the taper of the bubble ejection hole 3 is not limited to the example illustrated in FIG. 4C. For example, as illustrated in FIG. 4D, the bubble ejection hole 3 may be left-right asymmetrical in a cross-section view.

For the size of the first opening 31 and the second opening 32 of the device 1c, the size of the smaller opening may be the same as the size of the first opening 31 and the second opening 32 illustrated as an example in the device 1a of the first embodiment. Further, while the thickness of the device 1c can also be the same thickness as illustrated as an example in the device 1a of the first embodiment, unlike the device 1a, the electric field is likely to concentrate in the smaller-sized opening in the device 1c. Therefore, the substrate 2 may be thicker than that of the device 1a as long as a bubble can be ejected while the thickness differs in accordance with the angle Z of the wall face 33 relative to the second opening 32 (or the diameter ratio or the area ratio between the first opening 31 and the second opening 32).

Fourth Embodiment of Device and Modified Example Thereof

Next, a device 1d according to a fourth embodiment and a modified example thereof will be described with reference to FIG. 5A to FIG. 5D. FIG. 5A is a top view of the device 1d, and FIG. 5B is a sectional view taken along a line X-X' of FIG. 5A. Further, FIG. 5C is a top view of the modified example of the device 1d, and FIG. 5D is a sectional view taken along a line X-X' of FIG. 5C. The device 1d and the modified example thereof are different from the device 1a of the first embodiment in further having a first chamber 5a and a second chamber 5b for filling the conductive liquid L and are the same as the first embodiment in other features.

In the example illustrated in FIG. 5A and FIG. 5B, the first chamber 5a of the device 1d includes a portion including at least the first opening 31 in the first face 21 of the substrate 2 and a chamber first member 51a arranged in contact with the first face 21. As long as the first chamber 5a includes the first opening 31, the arranged position of the chamber first member 51a is not particularly limited and can be any position on the first face 21. The second chamber 5b includes a portion including at least the second opening 32 in the second face 22 of the substrate 2 and a chamber second member 51b arranged in contact with the second face 22. As long as the second chamber 5b includes the second opening 32, the arranged position of the chamber second member 51b is not particularly limited and can be any position on the second face 22. With the first chamber 5a and the second chamber 5b being filled with the conductive liquid L, the first opening 31 and the second opening 32 can be in contact with the conductive liquid L.

The chamber first member 51a and the chamber second member 51b may be an electrically and chemically inactive material. For example, a glass, a sapphire, a ceramic, a resin, a rubber, an elastomer, $SiO_2$, SiN, $Al_2O_3$, or the like can be used. The chamber first member 51a and the chamber second member 51b can be adhered to the substrate 2 in a liquid-tight manner by using an adhesive agent or the like.

Note that, in the example illustrated in FIG. 5A and FIG. 5B, either the first chamber 5a or the second chamber 5b may be of a size that prevents the filled conductive liquid L from being leaked out by surface tension. In such a case, since a processing target can be brought into contact with the filled conductive liquid L and bubbles can be ejected to the processing target, an advantage of being capable of ejecting bubbles to any processing target at any place can be obtained.

Next, the modified example of the device 1d illustrated in FIG. 5C and FIG. 5D is the same as the device 1d illustrated in FIG. 5A and FIG. 5B except that the substrate 2 is inserted in a casing and that a method of use is different from that for the device 1d illustrated in FIG. 5A and FIG. 5B. More specifically, the method of use of the modified example of the device 1d is different from that for the device 1d of the embodiment in that the conductive liquid L is filled from the top of the first chamber 5a and the second chamber and a processing target is inserted from the top in a direction in which bubbles are ejected. Note that, as is clear from FIG. 5A to FIG. 5D, when "chamber first member 51a" and "chamber second member 51b" are referred to in the present specification, the "chamber first member 51a" and "chamber second member 51b" each mean a part formed of both a separate member and a divided portion of a single member.

Note that, in FIG. 5A to FIG. 5D, although not illustrated, the first electrode may be arranged in the first chamber 5a, and the second electrode may be arranged in the second chamber 5b. In such a case, the position of the first electrode is not particularly limited as long as it is a place on either the chamber first member 51a or the first face 21 where the first electrode can be in contact with the conductive liquid L when the conductive liquid L is filled. Similarly, the second electrode may be arranged at any place on either the chamber second member 51b or the second face 22 where the second electrode can be in contact with the conductive liquid L when the conductive liquid L is filled.

The device 1a to the device 1d (and the modified example) exemplified above are mere examples, and some exemplified embodiments may be combined. For example, the tapered bubble ejection hole 3 of the third embodiment may be employed to the device 1b of the second embodiment and the device 1d of the fourth embodiment. Further, the first chamber 5a and the second chamber 5b of the fourth embodiment may be employed to the device 1b of the second embodiment and the device 1c of the third embodiment. Further, the first electrode 4a may be arranged on the first face 21 of the devices 1a to 1c of the first to third embodiments, and the second electrode 4b may be arranged on the second face 22. In addition, an appropriate change may be made as long as the object disclosed in the present application can be achieved.

[Embodiment of Bubble Ejection Apparatus]

Figures 5, 6:
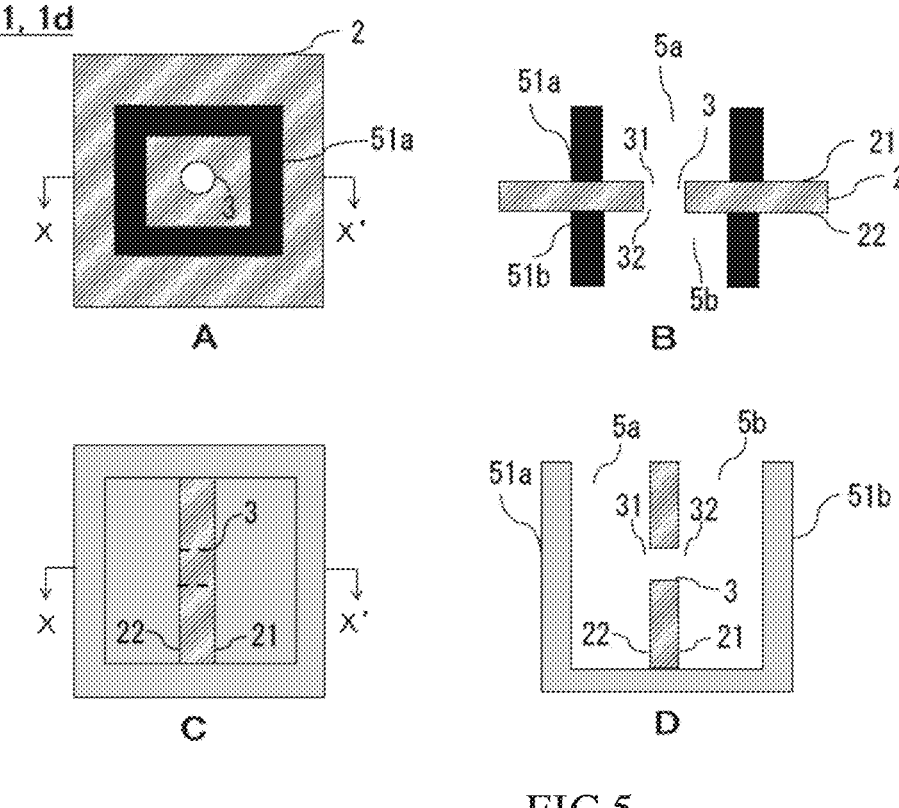
FIG. 6 is a diagram illustrating an overview of a bubble ejection apparatus 10.

An embodiment of a bubble ejection apparatus 10 will be described with reference to FIG. 6. FIG. 6 is a diagram illustrating an overview of the bubble ejection apparatus 10. The bubble ejection apparatus 10 can be produced by combining the bubble ejecting device 1 and an electric output mechanism 6. Note that FIG. 6 illustrates an example using the bubble ejecting device 1a. The electric output mechanism 6 can include at least a power supply device 61, the first electrode 4a, the second electrode 4b, and electric wires 63 used for forming a circuit with the power supply device 61, the first electrode 4a, and the second electrode 4b. Note that, when the first electrode 4a and the second electrode 4b are arranged as components of the device 1, the electric output mechanism 6 may include neither the first electrode 4a nor the second electrode 4b.

The bubble ejection apparatus 10 may be provided with a non-inductive resistor 64, a voltage amplifier circuit (not illustrated), an input/output port (Digital Input Output (DIO)) 65, a control device 66 such as a PC that controls the power supply device 61, or the like, if necessary. The electric output mechanism 6 may be produced by preparing the components described above or may be produced by embedding the non-inductive resistor 64, the input/output port 65, or the like into a conventional electric circuit used for an electrical scalpel.

The conductive material forming the first electrode 4a and the second electrode 4b is not particularly limited as long as it conducts electricity and can be used as an electrode, and the conductive material may be a metal, for example, gold, silver, copper, aluminum, or the like, an alloy in which a small amount of tin, magnesium, chromium, nickel, zirconium, iron, silicon, or the like is added to the above metal, or the like.

As the power supply device 61, a general commercial AC power supply device can be used. The current, the voltage, and the frequency output from the electric output mechanism 6 to the first electrode 4a and the second electrode 4b are not particularly limited as long as a bubble can be ejected from the bubble ejection hole 3 into the conductive liquid L. For example, the current may be 1 mA to 500 mA or 50 mA to 200 mA to prevent unsuccessful bubble generation or dielectric breakdown of the substrate 2. The voltage may be, for example, 200 V to 4000 V or 600 V to 1800 V to prevent difficulty in bubble generation or dielectric breakdown of the substrate 2. The pulse width is preferably 500 ns to 1 ms and more preferably 1 μs to 100 μs. If the pulse width is shorter than 500 ns, a bubble is unable to be ejected, and if the pulse width is longer than 1 ms, a bubble is not suitably ejected. Note that the current, the voltage, the pulse width, or the like can be suitably adjusted in accordance with the material and the thickness of the substrate 2, the size of the first opening 31 and the second opening 32, or the like.

[Embodiment of Bubble Ejection Method]

Figure 7:
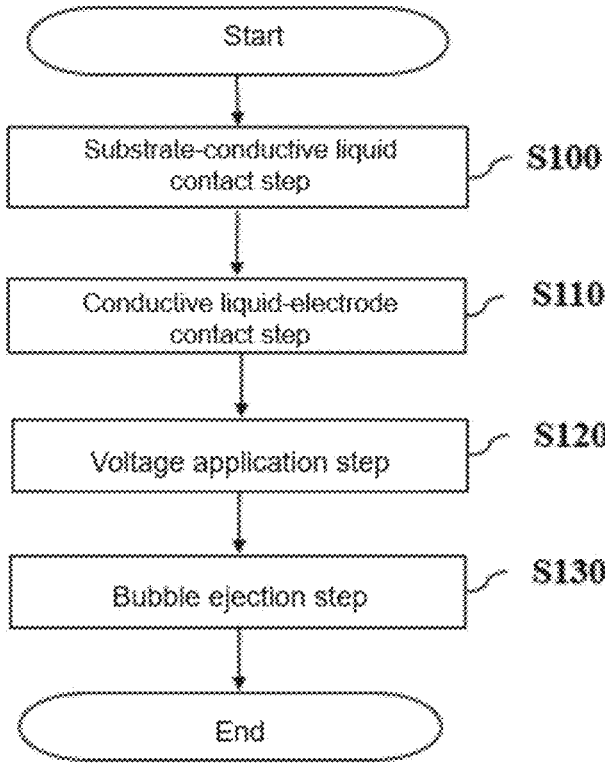
FIG. 7 is a flowchart illustrating a procedure of a bubble ejection method.

An embodiment of a bubble ejection method will be described with reference to FIG. 6 and FIG. 7. FIG. 7 is a flowchart illustrating a procedure of the bubble ejection method. The bubble ejection method includes a substrate-conductive liquid contact step (S100), a conductive liquid-electrode contact step (S110), a voltage application step (S120), and a bubble ejection step (S130).

In the substrate-conductive liquid contact step (S100), a portion including at least the first opening 31 and the second opening 32 of the device 1a is brought into contact with the conductive liquid L. In the example illustrated in FIG. 6, the conductive liquid L can be first dripped onto a processing target 7, the device 1a can be arranged above the conductive liquid L, and the conductive liquid L can be further dripped onto the device 1a. Note that, when a device with the first and second chambers is used as the device 1, the conductive liquid L can be filled in the first chamber and the second chamber. The conductive liquid L is not particularly limited as long as it conducts electricity and may be, for example, water, a solution in which a metal salt or the like are dissolved in water, or the like.

In the conductive liquid-electrode contact step (S110), the first electrode 4a is brought into contact with the conductive liquid L on the first opening 31 side, and the second electrode 4b is brought into contact with the conductive liquid L on the second opening 32 side. Note that, when a device having the first electrode 4a and the second electrode 4b in advance is used or when the first electrode 4a is arranged in advance in the first chamber and the second electrode 4b is arranged in advance in the second chamber, the substrate-conductive liquid contact step (S100) and the conductive liquid-electrode contact step (S110) may be performed simultaneously. Therefore, in the present specification, the reference to "including "the substrate-conductive liquid contact step (S100)" and "the conductive liquid-electrode contact step (S110)"" includes a case of performing "the substrate-conductive liquid contact step (S100)" and "the conductive liquid-electrode contact step (S110)" separately and a case of performing these steps simultaneously.

In the voltage application step (S120), a voltage is applied between the first electrode 4a and the second electrode 4b. Then, in the bubble ejection step (S130), a bubble that has grown in the bubble ejection hole 3 is ejected.

As disclosed in Patent Literature 1 and Patent Literature 2, by ejecting fine bubbles to a processing target, it is possible to cut (perform local ablation on) a processing target and introduce an injection substance to (perform local injection on) a processing target. Further, as illustrated in Examples described later, with a use of the device according to the embodiment, a silicon substrate was successfully cut. Therefore, the bubble ejection apparatus 10 can be used as a local ablation apparatus or a local injection apparatus, for example. Further, when a plating liquid is used as the conductive liquid, the bubble ejection apparatus 10 can be used as a plating apparatus. Further, the bubble ejection method can be used as a local ablation method, a local injection method, or a plating method, for example.

The processing target 7 is not particularly limited as long as it is an object on which the local ablation, the local injection, or the plating can be performed, for example, as described above. The processing target 7 may be, for example, an animal cell such as a stem cell, a skin cell, a mucosal cell, a hepatocyte, an islet cell, a nerve cell, a chondrocyte, an endothelial cell, an epithelial cell, a bone cell, a muscle cell, an egg cell, or the like isolated from a tissue of a human or a non-human animal, a plant cell, an insect cell, or a microbial cell such as *E. coli*, a yeast, and a mold, or the like; a relatively hard biological sample such as a rice or plant cell; a resin substrate using silicon, glass epoxy, polyester, polyimide, BT resin, and a resin such as thermosetting polyphenylene ether; an inorganic substrate using an inorganic material such as an alumina (ceramics) substrate; a silicon wafer or a metal substrate of aluminum, copper, or the like; a metal base substrate in which an insulating layer is stacked on the metal substrate and a copper foil that is a conductor is further stacked thereon; or the like.

Each embodiment will be specifically described below with Examples, however, these Examples are merely provided for references of specific aspects thereof. These illustrations are not intended to limit or restrict the scope of the invention.

EXAMPLES

Example 1

A device and a bubble ejection apparatus were produced by the following procedure, and a bubble ejection method was implemented by using the produced bubble ejection apparatus.

[Production of Device]

A polyimide film (polyimide tape by AS ONE Corporation) (thickness of 30 μm) was used for the substrate 2, and a substantially cylindrical bubble ejection hole 3 having a diameter of about 25 μm was formed by using a UV laser (MD-U by Keyence Corporation). Next, the substrate 2 was arranged in a box type chamber member (acrylic resin by Formlabs) as illustrated in FIG. 5D, and thereby the device of Example 1 including the first chamber and the second chamber was produced.

[Production of Bubble Ejection Apparatus]

The first electrode 4a and the second electrode 4b were produced by using copper wires (EggsSTORE, diameter of 2 mm). General electrical scalpel power supply Hyfrecator2000 (by ConMed Corporation) was used for the power supply device, the produced first electrode 4a and second electrode 4b were electrically connected by using electric wires, and the bubble ejection apparatus 10 was produced.

[Implementation of Bubble Ejection Method]

The first chamber 5a and the second chamber 5b of the produced device were filled with a conductive liquid (0.9 wt % sodium chloride aqueous solution). Further, the first electrode 4a was inserted in the first chamber 5a so as to be in contact with the conductive liquid, and the second electrode 4b was inserted in the second chamber 5b so as to be in contact with the conductive liquid. Next, the output condition of the power supply device was set such that an applied voltage was 800 V, the number of times of voltage application was one, and the pulse width was about 1 μs, and electrical power was output to the first electrode 4a and the second electrode 4b. The ejection of a bubble was observed by using a high-speed camera (VW-9000 by Keyence Corporation).

Figure 8:
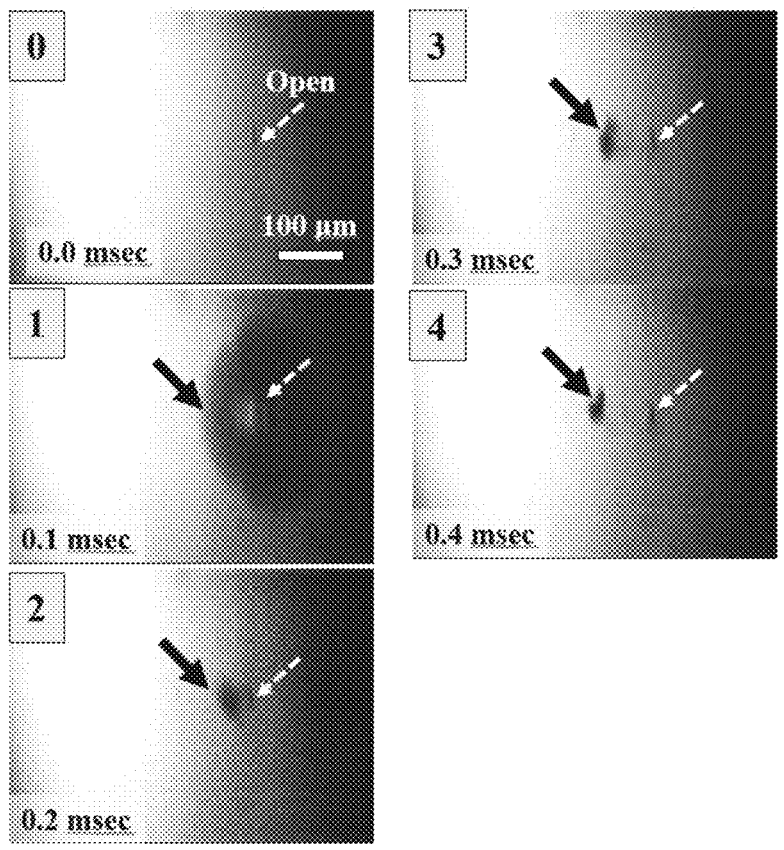
FIG. 8 illustrates photographs substitute for drawing, which are photographs in which generation of the bubble B is captured by a high-speed camera in Example 1.

FIG. 8 illustrates photographs when generation of the bubble B was captured by a high-speed camera. In the photographs, each dashed-line arrow indicates the first opening (Open) of the bubble ejection hole 3, and each solid-line arrow indicates a bubble. The numerical value on the lower part of each photograph represents time from electrical output. As is clear from photographs 0 to 4, it was confirmed that, with the use of the device produced in Example 1, a bubble was ejected from the first opening (Open) of the bubble ejection hole 3. Note that, when the first opening and the second opening have the same size, the opening included in the photograph is defined as the first opening. The same applies to the following Examples. Further, although description will be omitted in the following Examples, the capturing angle of the camera was suitably adjusted in accordance with the purpose of each Example.

Example 2

Next, an experiment of bubble ejection was performed with the device in which a plurality of bubble ejection holes 3 were formed.

[Production of Device]

The device was produced by the same procedure as that in Example 1 except that three bubble ejection holes 3 were made at three positions such that the diameter of each bubble ejection hole 3 was about 100 μm and the spacing between adjacent bubble ejection holes 3 was about 600 μm.

[Production of Bubble Ejection Apparatus and Implementation of Bubble Ejection Method]

Figure 9:
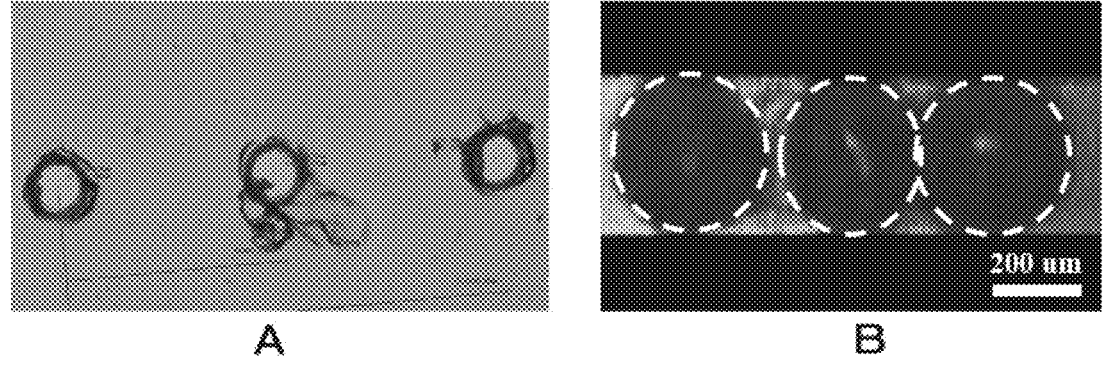
FIG. 9 illustrates photographs substitute for drawing.

Next, a bubble ejection apparatus was produced and a bubble ejection method was implemented by the same procedure as that in Example 1 except that the device produced in Example 2 was used instead of the device of Example 1. FIG. 9A is a photograph of the device of Example 2 captured from the top, and FIG. 9B is a photograph after electrical output in which each dashed-line circle indicates a bubble.

As illustrated in FIG. 9B, it was confirmed that the generated bubble grew to cover three opening parts and the bubbles were then ejected. From the above result, it was confirmed that bubbles can be ejected by using the device in which a plurality of bubble ejection holes 3 are formed.

Examples 3 and 4

Next, an experiment to observe how the taper of the bubble ejection hole 3 influences ejection of a bubble was performed.
[Production of Device]
First, conical molds in which the angles Z illustrated in FIG. 4C were 55 degrees (Example 3) and 70 degrees (Example 4) were produced by using a 3D printer. Next, PDMS (Sylgard 184 by Toray Dow Corning Inc.) was poured into the produced molds and cured, the molds were separated, and the devices of Example 3 and Example 4 were produced. The sizes of the produced device were as follows.

Example 3

Angle Z of the taper: 55 degrees
Thickness: 5 mm
Diameter of the first opening: 100 μm
Diameter of the second opening: 6 mm

Example 4

Figure 10:
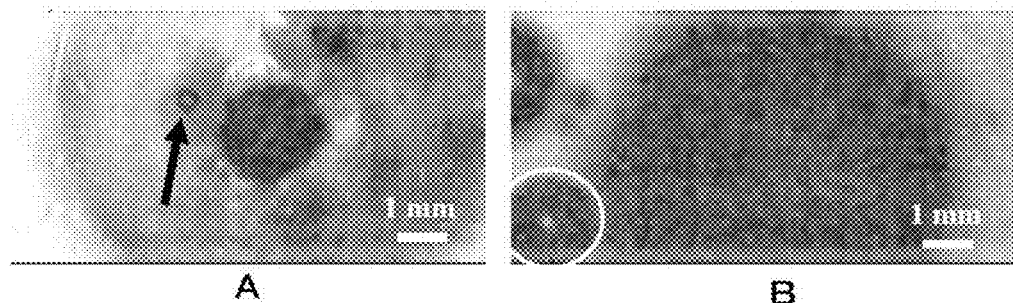
FIG. 10 illustrates photographs substitute for drawing.

Angle Z of the taper: 70 degrees
Thickness: 3 mm
Diameter of the first opening: 100 μm
Diameter of the second opening: 2 mm
[Production of Bubble Ejection Apparatus and Implementation of Bubble Ejection Method]
Next, a bubble ejection apparatus was produced and a bubble ejection method was implemented by the same procedure as that in Example 1 except that the devices produced in Example 3 and Example 4 were used instead of the device of Example 1. FIG. 10A is a photograph from the first opening side taken when the device of Example 3 was used, and FIG. 10B is a photograph from the first opening side taken when the device of Example 4 was used, in which each ejected bubble is indicated by the arrow in FIG. 10A and the portion surrounded by the white circle in the photograph of FIG. 10B. As represented by the photographs, ejection of a bubble was confirmed in both the devices of Example 3 and Example 4. Further, it was confirmed that a bubble was ejected from the smaller-sized first opening even when the experiment was performed with the first electrode 4a and the second electrode 4b being exchanged, that is, with the positive electrode and the negative electrode being exchanged.

As illustrated in Examples described later, a thicker device requires a larger voltage for ejecting a bubble. In other words, under the same electrical output condition, a thicker device makes it more difficult to eject a bubble. On the other hand, in the devices of Example 3 and Example 4, the device of Example 3 generated a larger bubble even though the device of Example 3 (thickness of 5 mm) is thicker than the device of Example 4 (thickness of 3 mm) under the same condition of the first opening size and the electrical output. From the above result, it was confirmed that a larger angle of the taper of the bubble ejection hole 3 (a larger size ratio of the second opening to the first opening) more facilitates ejection of a bubble.

Example 5

Next, a bubble ejection experiment was performed with a changed shape of the bubble ejection hole 3.

Figure 11:
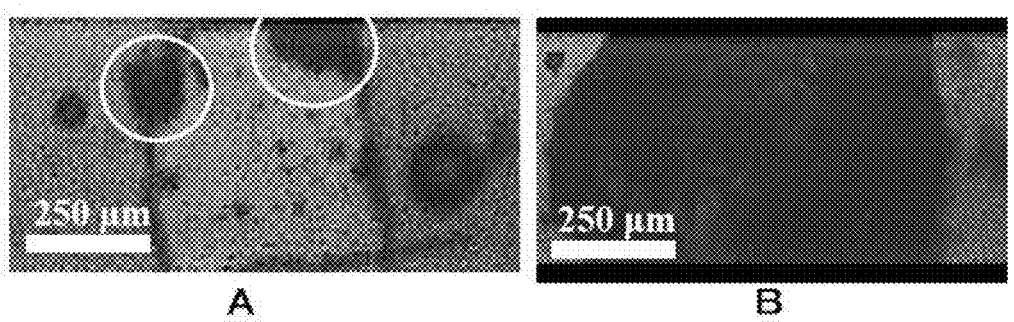
FIG. 11 illustrates photographs substitute for drawing.

[Production of Device]
A device having substantially square first opening and second opening was produced by the same procedure as that in Example 1 except that processing was performed by using a cutter instead of a drill. One side of the first opening and the second opening was about 500 μm.
[Production of Bubble Ejection Apparatus and Implementation of Bubble Ejection Method]
Next, a bubble ejection apparatus was produced and a bubble ejection method was implemented by the same procedure as that in Example 1 except that the device of Example 5 was used instead of the device of Example 1. FIG. 11A is a photograph from the first opening side taken immediately after electrical output, and FIG. 11B is a photograph from the first opening side taken after a while of the electrical output.

As illustrated in the portions each surrounded by a circle of FIG. 11A, it was confirmed that a bubble was generated from a corner where an electric field is likely to concentrate, grew to cover the whole first opening as illustrated in FIG. 11B, and was then ejected. From the above result, it was confirmed that a bubble is ejected even when the shape of the bubble ejection hole 3 (the first opening and the second opening) is a polygonal. Further, it was confirmed that, when a bubble is ejected, a bubble generated from the circumference of the bubble ejection hole 3, in particular, a portion where an electric field is likely to concentrate grows, covers the whole first opening, and is then ejected.

Example 6

Figure 12:
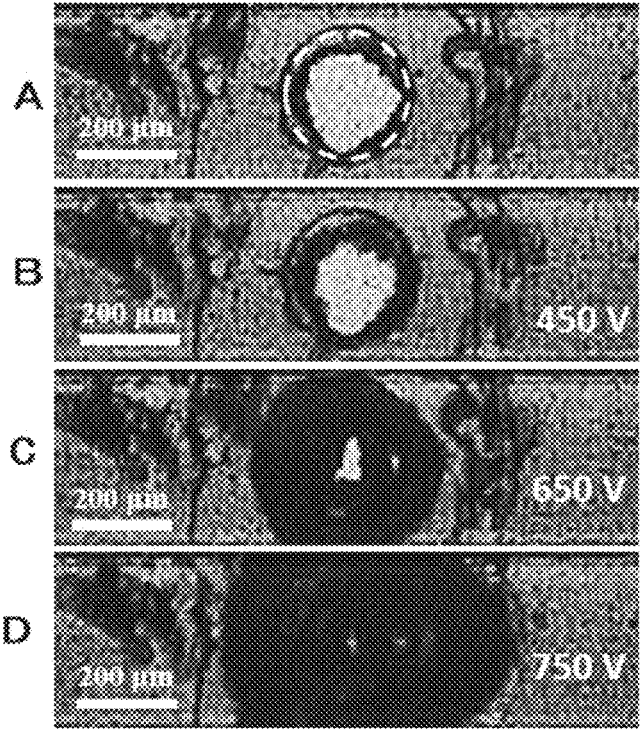
FIG. 12 illustrates photographs substitute for drawing.

Next, an experiment to examine the relationship between the size of the bubble ejection hole (the first opening) and the applied voltage was performed.
[Production of Device]
A device having substantially circular first opening and second opening was produced by the same procedure as that in Example 1 except for a change in the drill shape. The diameter of the first opening and the second opening was about 200 μm.
[Production of Bubble Ejection Apparatus and Implementation of Bubble Ejection Method]
Next, a bubble ejection apparatus was produced and a bubble ejection method was implemented by the same procedure as that in Example 1 except that the device of Example 6 was used instead of the device of Example 5 and that the applied voltage was changed to 450 V, 650 V, and 750 V. FIG. 12A is a photograph from the first opening side taken before a voltage is applied, FIG. 12B is a photograph from the first opening side taken after a voltage of 450 V is applied, FIG. 12C is a photograph from the first opening side taken after a voltage of 650 V is applied, and FIG. 12D is a photograph from the first opening side taken after a voltage of 750 V is applied.

The portion surrounded by the dashed-line white circle of FIG. 12A corresponds to the first opening. As is clear from FIG. 12A, before the electrical output, the conductive liquid was filled in the bubble ejection hole 3. Further, as illustrated in FIG. 12B to FIG. 12D, because the conductive liquid inside the bubble ejection hole 3 was viewed smaller as the applied voltage was increased, it was confirmed that a bubble (the black portion around the conductive liquid in the photograph) grew from the circumferential part of the bubble ejection hole 3. Further, when the voltage of 750 V was applied, the whole bubble ejection hole 3 was covered with a bubble as illustrated in FIG. 12D, and ejection of the bubble was also confirmed. On the other hand, when 450 V was applied as seen in FIG. 12B and when 650 V was applied as seen in FIG. 12C, no bubble was ejected.

From the above result, it was confirmed that a larger size of the first opening requires a larger voltage for covering the bubble ejection hole 3 with a bubble and further ejecting the bubble. It was therefore confirmed that the voltage can be suitably adjusted in accordance with the size of the bubble ejection hole 3 (first opening) required in processing of a processing target.

Examples 7 and 8

Next, an experiment to examine the relationship between the thickness of the substrate 2 (the length of the bubble ejection hole 3) and the applied voltage was performed.
[Production of Device]

Two types having a thickness of the substrate 2 of 200 μm (Example 7) and 300 μm (Example 8) were prepared by using a styrole resin (clear plastic plate by TAMIYA INC.) as the material of the substrate 2. A substantially cylindrical bubble ejection hole 3 having a diameter of 200 μm was formed by using a drill.
[Production of Bubble Ejection Apparatus and Implementation of Bubble Ejection Method]

Figure 13:
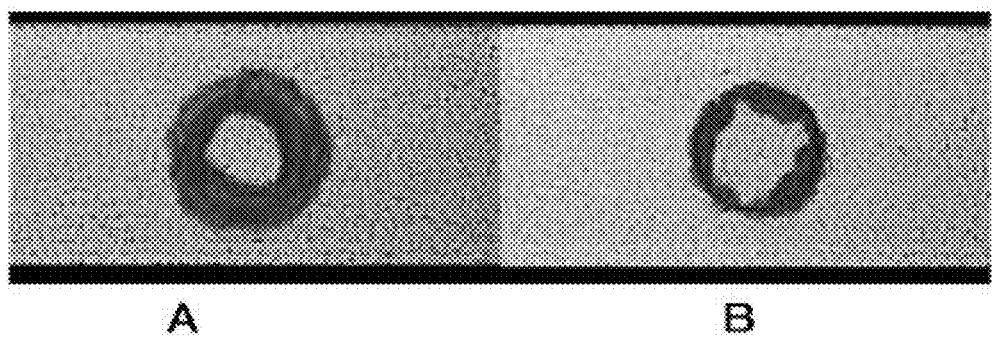
FIG. 13 illustrates photographs substitute for drawing.

Next, a bubble ejection apparatus was produced and a bubble ejection method was implemented by the same procedure as that in Example 1 except that the device of Examples 7 and 8 were used instead of the device of Example 1 and that the applied voltage was 1200 V. FIG. 13A is a photograph of the device of Example 7 from the first opening side taken after a while of application of a voltage, and FIG. 13B is a photograph of the device of Example 8 from the first opening side taken after a while of application of a voltage.

As illustrated in FIG. 13A and FIG. 13B, a more amount of the conductive liquid remained inside the bubble ejection hole 3 in the device of FIG. 13B having the thicker substrate 2, in other words, less bubbles (the black portion of the photograph) grew from the circumference part of the bubble ejection hole 3. Note that, when the applied voltage was increased up to 1500 V, ejection of a bubble was confirmed in both Examples 7 and 8.

From the above result, it was confirmed that a thicker substrate 2 (having a longer bubble ejection hole 3) requires a larger voltage for covering the bubble ejection hole 3 with a bubble and further ejecting the bubble. It was therefore confirmed that the thickness of the substrate 2 can be suitably adjusted in accordance with the condition such as an applied voltage.

Example 9

Next, experiments were performed with different types of the substrate 2.
[Production of Device]

The bubble ejection hole 3 was formed by using a glass (MICRO COVER GLASS No. 1 by Matsunami Glass Industry Co.) as the material of the substrate 2 and using a UV laser. Note that the bubble ejection hole 3 was shaped tapered due to influence of heat of the UV laser processing. The diameter of the first opening was about 70 μm, and the diameter of the second opening was about 200 μm.
[Production of Bubble Ejection Apparatus and Implementation of Bubble Ejection Method]

Figure 14:
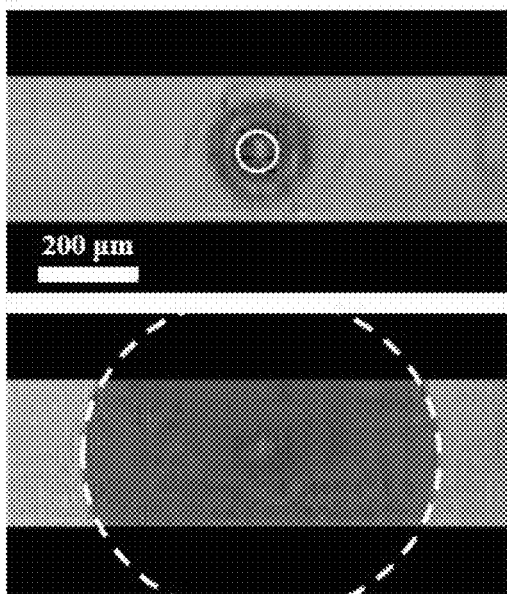
FIG. 14 illustrates photographs substitute for drawing.

Next, a bubble ejection apparatus was produced and a bubble ejection method was implemented by the same procedure as that in Example 1 by using the device of Example 9 instead of the device of Example 1. FIG. 14A is a photograph captured from the first opening side before a voltage is applied. Note that the circle in the photograph represents the first opening, and the discolored part around the first opening is a portion affected by heat, and the outer circumference of the discolored part corresponds to the size of the second opening. FIG. 14B is a photograph captured from the first opening side after the voltage is applied, and the portion surrounded by a dashed line represents a bubble that has grown to cover the first opening. Ejection of a bubble was then confirmed.

From the above result, it was confirmed that a dielectric material other than a resin can be used as the substrate 2 to eject a bubble.

Example 10

Next, an experiment of cutting a processing target was performed.
[Production of Device]

The device was produced by the same procedure as in Example 1 except that a bubble ejection hole having a diameter of about 100 μm was formed by thrusting using a tungsten wire.
[Production of Bubble Ejection Apparatus and Implementation of Bubble Ejection Method]

Next, a bubble ejection apparatus was produced by the same procedure as that in Example 1 by using the device of Example 10 instead of the device of Example 1. Next, the bubble ejection method was implemented by the same procedure as that in Example 1 except that the output was 2000 V, a silicon wafer (one-side mirror wafer, inch, thickness of 525±25 μm by Kabusikigaisha Matsunami Seisakusho) was arranged in front of the bubble ejection hole, and a voltage was applied for multiple times while the position of the silicon wafer is shifted.

Figure 15:
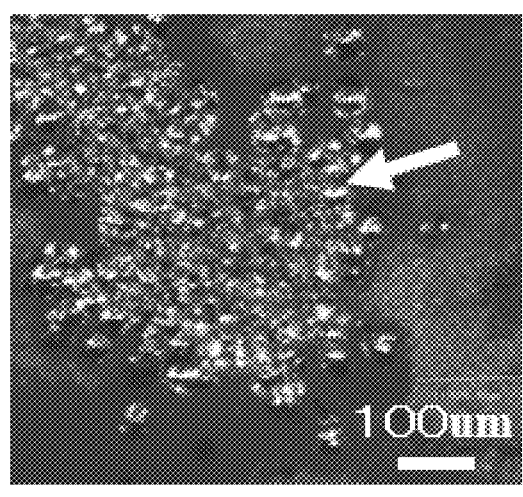
FIG. 15 is a photograph substitute for drawing, which is a photograph of a silicon wafer with which a bubble was collided in Example 10.

FIG. 15 is a photograph of a silicon wafer with which a bubble was collided in Example 10, and the part indicated by the arrow is a hole formed in the silicon wafer. From the above result, it was confirmed that the device, the bubble ejection apparatus, and the bubble ejection method according to the embodiments can be used for cutting a processing target or the like.

Example 11

Next, devices having different thicknesses of the substrate 2 (lengths of the bubble ejection hole 3) and different diameters of the bubble ejection hole 3 were prepared, and the value of an electric field of the bubble ejection hole 3 when a bubble was ejected was examined.
[Production of Device]

The devices were produced by the same procedure as that in Example 1 except that the substrates 2 having thicknesses of 25 μm, 50 μm, and 75 μm were prepared and that the bubble ejection holes 3 having diameters of about 100 μm, about 200 μm, about 300 μm, and about 400 μm were formed in respective substrates 2.
[Production of Bubble Ejection Apparatus and Implementation of Bubble Ejection Method]

Next, a bubble ejection apparatus was produced and a bubble ejection method was implemented by the same procedure as that in Example 1 except that various devices having different thicknesses and different diameters of the bubble ejection hole produced in Example 11 were used instead of the device of Example 1. Note that, in the bubble ejection method, the applied voltage was changed for each produced device, and the applied voltage when ejection of a bubble started was examined.

Figure 16:
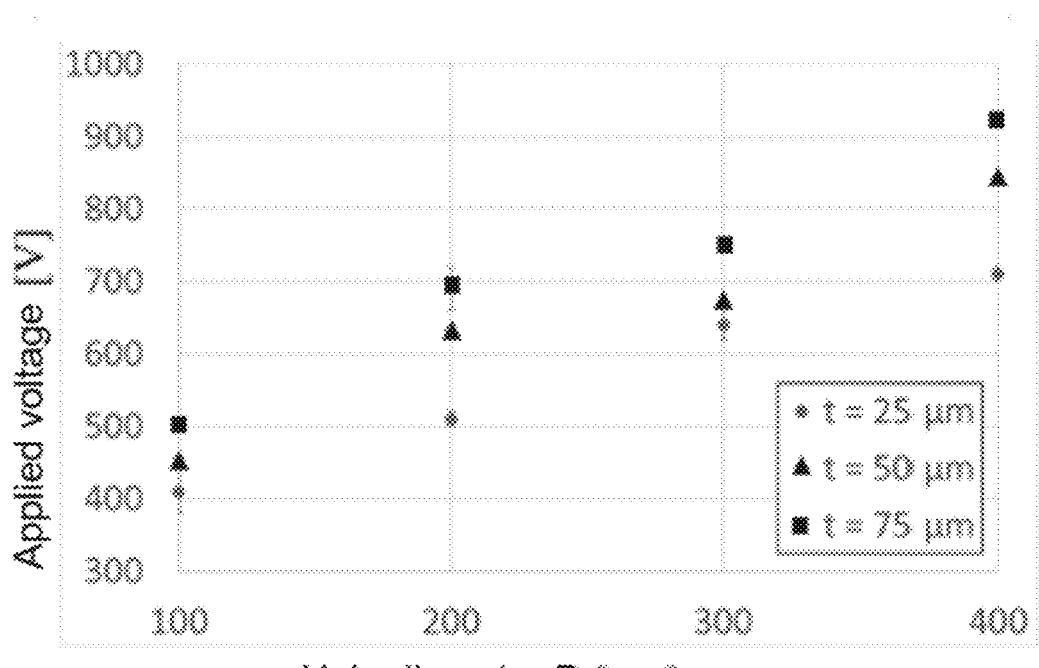
FIG. 16 is a graph illustrating a relationship between the diameter of a bubble ejection hole 3 of various devices (hole diameter; horizontal axis) and the applied voltage when ejection of a bubble started (vertical axis) in Example 11.

FIG. 16 is a graph illustrating the relationship between the diameter of the bubble ejection hole 3 of respective devices (hole diameter; horizontal axis) and the applied voltage when ejection of a bubble started (vertical axis). As indicated in FIG. 16, it was confirmed that the voltage required for ejecting a bubble was lower for a smaller diameter of the bubble ejection hole 3 and that the voltage required for ejecting a bubble was lower for a smaller thickness of the substrate 2.

Figure 17:
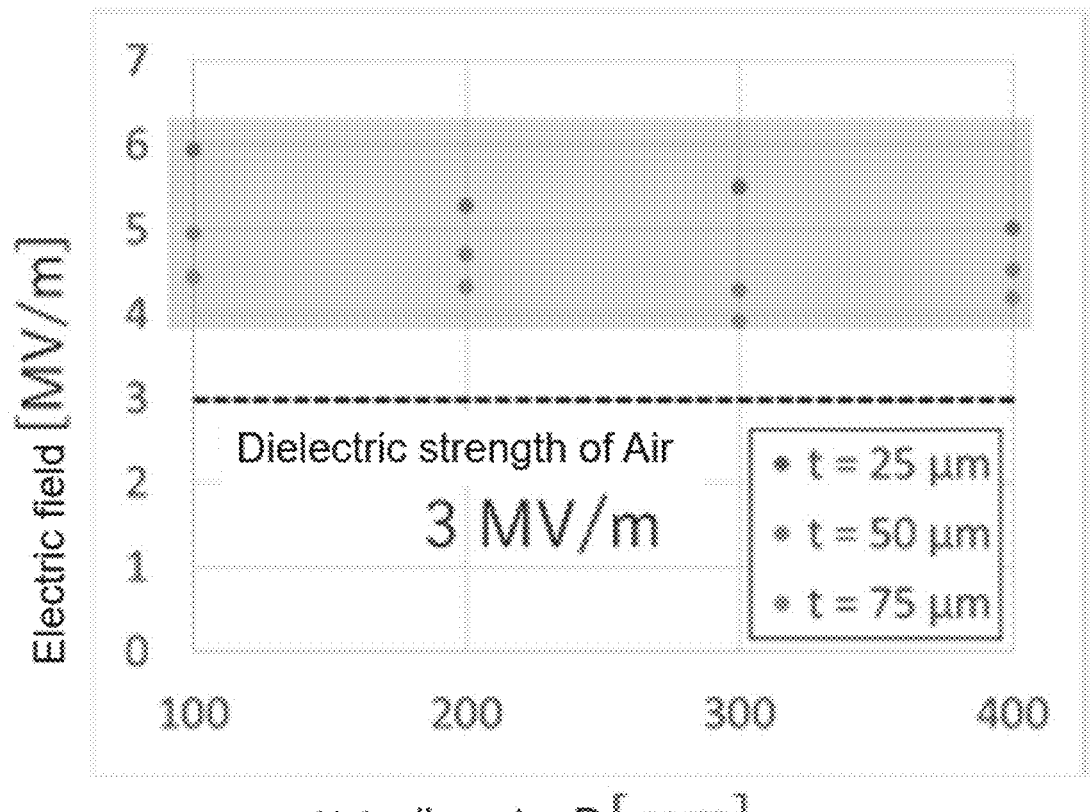
FIG. 17 is a graph illustrating electric field values of the bubble ejection hole 3 when a bubble is ejected in which the electric field value is analyzed by a finite element method in Example 11.

Next, for respective devices, the value of an electric field of the bubble ejection hole 3 when a bubble was ejected was analyzed by using a finite element method based on the thickness of the device, the hole diameter of the bubble ejection hole 3, and the applied voltage when the ejection of a bubble started. Note that COMSOL Multiphysics (registered trademark) was used as analysis software of the finite element method. FIG. 17 illustrates the analysis result. As indicated in FIG. 17, it was confirmed that, while it may depend on the thickness of the substrate 2 and the size of the bubble ejection hole 3, a bubble can be ejected from the bubble ejection hole 3 when an electric field of about 4 MV/m or greater is generated in the bubble ejection hole 3. Further, from the result illustrated in FIG. 16 and FIG. 17, it was revealed that the thickness of the substrate can be increased when a material having a small dielectric strength is used as the substrate 2.

INDUSTRIAL APPLICABILITY

The bubble ejecting device disclosed in the present application can be easily produced by forming a bubble ejection hole in a substrate formed of a dielectric so as to penetrate the substrate. Further, since the bubble ejection hole is formed so as to penetrate the substrate, a bubble is ejected from the surface of the substrate. Thus, unlike the conventional bubble ejection port, the bubble ejection hole is less likely to break. Therefore, the present invention is useful in fields that require local processing, such as a field of semiconductor manufacturing, a field of information processing, a field of livestock, agriculture, forestry, and fisheries, or the like.

LIST OF REFERENCES

1, 1*a*, 1*b* bubble ejecting device
2 substrate
3 bubble ejection hole
4*a* first electrode
4*b* second electrode
5*a* first chamber
5*b* second chamber
6 electric output mechanism
7 processing target
10 bubble ejection apparatus
21 first face
22 second face
31 first opening
32 second opening
33 wall face (wall face line)
51*a* chamber first member
51*b* chamber second member
61 power supply device
63 electric wire
64 non-inductive resistor
65 input/output port (Digital Input Output (DIO))

66 control device
B bubble
L conductive liquid
Z angle

The invention claimed is:

1. A bubble ejection method using a bubble ejecting device, wherein the bubble ejecting device comprises:
    a substrate formed of a dielectric,
    at least one bubble ejection hole formed so as to penetrate through a first face and a second face, which is a face opposite to the first face, of the substrate,
    a first opening formed at a position of the first face at which the bubble ejection hole penetrates, and
    a second opening formed at a position of the second face at which the bubble ejection hole penetrates, the bubble ejection method comprising:
    disposing a conductive liquid onto a processing target;
    bringing a portion including at least the first opening and the second opening into contact with the conductive liquid;
    bringing a first electrode into contact with the conductive liquid on the first opening side and bringing a second electrode into contact with the conductive liquid on the second opening side;
    applying a voltage between the first electrode and the second electrode;
    ejecting a whole bubble from the bubble ejection hole onto the processing target through the conductive liquid disposed outside the bubble ejection hole.

2. The bubble ejection method according to claim 1, wherein at least two or more bubble ejection holes are formed.

3. The bubble ejection method according to claim 1, wherein a size of the first opening and a size of the second opening are different from each other.

4. The bubble ejection method according to claim 1, wherein a dielectric strength of the dielectric is greater than or equal to 10 MV/m.

5. The bubble ejection method according to claim 1, wherein the substrate is formed of a flexible material.

6. The bubble ejection method according to claim 2, wherein a dielectric strength of the dielectric is greater than or equal to 10 MV/m.

7. The bubble ejection method according to claim 3, wherein a dielectric strength of the dielectric is greater than or equal to 10 MV/m.

8. The bubble ejection method according to claim 2, wherein the substrate is formed of a flexible material.

9. The bubble ejection method according to claim 3, wherein the substrate is formed of a flexible material.

10. The bubble ejection method according to claim 4, wherein the substrate is formed of a flexible material.

11. The bubble ejection method according to claim 1, wherein a material forming the substrate is at least one selected from the group consisting of polyimide, polystyrene, a glass, an epoxy resin containing no filler, an epoxy resin containing a silica filler, and an epoxy resin containing a glass fiber filler.

12. The bubble ejection method according to claim 4, wherein a material forming the substrate is at least one selected from the group consisting of polyimide, polystyrene, a glass, an epoxy resin containing no filler, an epoxy resin containing a silica filler, and an epoxy resin containing a glass fiber filler.

13. The bubble ejection method according to claim 10, wherein a material forming the substrate is polyimide.

14. The bubble ejection method according to claim 1, wherein the processing target is cut by ejecting the ejected bubbles onto the processing target.

15. The bubble ejection method according to claim 14, wherein a material forming the substrate is at least one selected from the group consisting of polyimide, polystyrene, a glass, an epoxy resin containing no filler, an epoxy resin containing a silica filler, and an epoxy resin containing a glass fiber filler.

16. The bubble ejection method according to claim 1, wherein the conductive liquid includes an injection substance, and wherein the injection substance is introduced to the processing target by ejecting the ejected bubbles onto the processing target.

17. The bubble ejection method according to claim 16, wherein a material forming the substrate is at least one selected from the group consisting of polyimide, polystyrene, a glass, an epoxy resin containing no filler, an epoxy resin containing a silica filler, and an epoxy resin containing a glass fiber filler.

18. The bubble ejection method according to claim 1, wherein the conductive liquid is a plating liquid, and wherein the processing target is plated by ejecting the ejected bubbles onto the processing target.

19. The bubble ejection method according to claim 18, wherein a material forming the substrate is at least one selected from the group consisting of polyimide, polystyrene, a glass, an epoxy resin containing no filler, an epoxy resin containing a silica filler, and an epoxy resin containing a glass fiber filler.

* * * * *